United States Patent [19]

Casey

[11] 4,161,514

[45] Jul. 17, 1979

[54] COMPOSITION AND METHOD FOR PREPARING SPECIMENS OF MICRO-ORGANISMS FOR MICROSCOPIC EXAMINATION

[76] Inventor: Dee O. Casey, 281 Maple St., Brevard, N.C. 28712

[21] Appl. No.: 766,229

[22] Filed: Feb. 7, 1977

Related U.S. Application Data

[63] Continuation-in-part of Ser. No. 655,385, Feb. 5, 1976, abandoned, which is a continuation-in-part of Ser. No. 277,909, Oct. 5, 1972, abandoned.

[51] Int. Cl.$^2$ .................... C12K 1/04; G01N 1/00; G01N 1/28; G01N 1/30
[52] U.S. Cl. ........................................ 424/3; 8/3; 8/94.1 R; 8/94.11; 8/96; 435/34; 424/75; 424/151
[58] Field of Search ................ 424/3, 52, 75, 151; 8/3, 94.1, 94.11, 96; 195/103.5 M

[56] References Cited

U.S. PATENT DOCUMENTS

| | | | |
|---|---|---|---|
| 2,015,062 | 9/1935 | Benjamin | 424/151 |
| 2,095,464 | 10/1937 | Chesnutt | 424/151 |
| 2,913,373 | 11/1959 | Weisz | 424/52 |
| 3,027,304 | 3/1962 | Robertson | 424/52 |

FOREIGN PATENT DOCUMENTS 675400  4/1939  Fed. Rep. of Germany ........... 424/151

OTHER PUBLICATIONS

Gregory, Uses & Applications of Chem. & Related Mat., The Guinn Co., NY, 1939, pp. 316, 317, 537.
Splatt, Biol. Abs., vol. 4, Mar. 1930, Ab. No. 7538.
Grey, Ency. of Micro & Microtech, VanNostrand-Reinhold Co., NY, 1973, pp. 175, 177.
Verona, Chem. Abs., vol. 30, 1936, p. 6778$^8$.
Conn, Biological Stains, Biotech Pub., Geneva, NY, 5th Ed., 1946, pp. 13, 118, 119, 291, 292.
Websters, Third New Int. Dict., unabridged, G & C Merriam Co., Springfield, Mass., 1963, p. 1642.

Primary Examiner—Anna P. Fagelson
Attorney, Agent, or Firm—Owen, Wickersham & Erickson

[57] ABSTRACT

A method is provided for preparing specimens of water containing micro-organisms, for microscopic viewing, employing a composition for immobilizing and also for staining the micro-organisms as an aqueous solution. The composition contains hydrofluoric acid and, advantageously, a small amount of malachite green dye.

15 Claims, No Drawings

COMPOSITION AND METHOD FOR PREPARING SPECIMENS OF MICRO-ORGANISMS FOR MICROSCOPIC EXAMINATION

REFERENCE TO RELATED APPLICATIONS

This application is a continuation-in-part of Ser. No. 655,385, filed Feb. 5, 1976, which was a continuation-in-part of Ser. No. 277,909, filed Oct. 5, 1972 both are abandoned.

BACKGROUND OF THE INVENTION

This invention concerns a composition for improving the miroscopic examination of microscopic living organisms and also a method for carrying out such examination.

Methods have been known for aiding in and improving the investigation and examination of microscopic organisms under the miroscope. Such organisms include, for instance, infusoria, protista and other motile micro-organisms, whether in fresh water or salt water, which are difficult to observe because of their motility and which it is desirable to immobilize on the viewing slide or the like. One such method has been to add methyl cellulose to the water containing the organism, but this method required physical or mechanical mixing of the methyl cellulose with the water containing the micro-organism, and this mixing tended to destroy or distort the organism.

An advantage of the present invention is that the composition mixes readily with the water containing the organism directly upon contact therewith and requires no physical agitation or mixing so that the micro-organism remains in a substantially intact and non-distorted state. It is a further advantage that the micro-organism, such as protista, is quickly immobilized, all motion being stopped by this composition and method. It is a particular advantage of this invention that the features of the micro-organism are brought out very clearly, more so than with the prior-art compositions and methods, enabling the investigator to see the organism's anatomical features, such as those of protista or other microorganisms with speed and precision. Thus, the examination is much more rapid than with methods heretofore known both because of the effect merely upon contact of the composition with the micro-organism and because of the clarity of the viewing field and such organism therein. Another advantage of the invention in its preferred form is that the viewing field is given a clear blue color, that is, azure in fresh water and turquoise in marine water, which is restful and pleasing to the eye and against which the micro-organism stands out unusually clearly. The solution of the invention can be stored indefinitely.

SUMMARY OF THE INVENTION

This invention concerns a composition which improves the viewing of micro-organisms under a microscope, by immobilizing or by staining or by immobilizing and staining microscopic living organisms, such as infusoria, protista, paramecia, and like organisms, without lysis or distortion of their form or shape. In other words, the structure of such organisms is maintained intact and, for example, such features as the cilia, nuclei, vacuoles, and trichocysts in paramecia can be observed with clarity. The invention also concerns a method for immobilizing and for staining such living organisms, for instance, for microscopic examination.

The composition of the present invention is an aqueous solution containing from about 0.025% to about 0.125% by weight hydrogen fluoride, HF (i.e., about 0.05% to about 0.25% of commercial hydrofluoric acid, which is a 50% concentration, approximately, thereof in water), and, preferably, an amount of malachite green $C_{23}H_{25}Cl\cdot N_2$, sufficient to provide a solution of pleasing pale color as background for viewing.

When studying fresh water organisms, the composition is an aqueous solution containing from about 0.035% to about 0.10% by weight HF in distilled water, and optimum results are often obtained with such composition containing about 0.05% by weight HF. When examining marine life organisms, the solution contains from 0.025% to 0.125% by weight HF in filtered sea water, and optimum results appear to be obtained with about 0.05% by weight thereof. Below the minimum amount of HF (0.035% in distilled water, 0.025% in salt water), the reaction is slow or is incomplete; and above the maximum amounts (0.10% in distilled water or 0.125% in salt water), the more fragile fresh water organisms tend to form bubble-like protrusions from the surface, followed by disintegration; or the marine organisms become distorted and some lysis occurs.

The invention is very useful in immobilizing as well as staining motile micro-organisms but is also useful in staining immotile micro-organisms, for microscopic examination, and the advantages of the invention are obtained because no agitation is required and the micro-organism structure is maintained. The specific gravity of the composition of the invention is about the same as that of the aqueous media in which protista or other micro-organisms grow, so that the liquids blend with each other very readily.

As noted, for examination of fresh water organisms, the water employed in the solution is distilled water; and when examining marine life, the water is filtered sea water.

The composition of this invention appears to be unique in its ability to immobilize the organisms in a manner giving optimum viewing characteristics. Methyl cellulose, not a stain, which has been used in the prior art in compositions for viewing micro-organisms, is a slowing agent but does not immobilize. It must be mixed mechanically and, in the process of agitation, the specimens are sometimes mutilated or destroyed.

I have found that neither hydrochloric acid nor fluosilicic acid work in my invention, in any concentration, nor do sulfuric acid, nitric acid, acetic acid, or citric acid. Sodium fluoride, calcium fluoride, acid fluoride or metal $(HF)_2$ compounds also are ineffective in the present invention, as are sodium chloride, potassium chloride, methyl alcohol, ethyl alcohol, sodium hydroxide, and potassium hydroxide.

The hydrofluoric acid is what achieves the immobilization and staining of the micro-organism, and, so far as immobilization is concerned, it (in the narrow range of concentration given) is sufficient. The immobilized organism can be viewed through the microscope. However, the specimen will stand out more clearly if the solution contains the malachite green.

The preferred composition of this invention immobilizes and stains the specimen simultaneously. Malachite green is an organic dye and pH indicator of the empirical formula shown above and is very soluble in water. Sufficient is added to provide a clear blue solution which enables a very clear view of the organisms under study. The addition of a small amount, e.g., about 0.000345% by weight, of this compound provides a composition yielding excellent results. The malachite green appears to work as a hydrogen-ion concentration or pH indicator. This enables the researcher to identify the fresh water chemical combination by the clear azure blue color, and the marine water chemical combination by the clear turquoise color. Both clear colors assist in viewing by providing a soft, restful background in the microscopic field.

I have been unable to find any other dye that helps. I have experimented with methylene blue, aniline red, eosin, aniline green, aniline blue, gentian violet, iodine, and commercial food colors—green, yellow, red, and blue. They tend to stain the impurities in the sample and to cloud the microscopic field, making it difficult or impossible to view minute anatomical structures. Malachite green does not interfere in this manner.

In preparing a specimen for miroscopic investigation, one drop of the solution of the invention is mixed with one equal drop of a specimen which is an aqueous suspension of the micro-organisms to be examined. The drop of such solution can be applied centrally of the surface, or in the center, of the specimen, and the result is instant immobilization of the microorganisms. The drop of such solution can alternatively be applied to or dropped at the side of the specimen for contrast viewing of mobile and immobile organisms, the drops blending at such side area only, so that the micro-organisms at the opposite side of the drop of specimen remain mobile while those in contact with the HF solution are immobilized.

DETAILED DESCRIPTION OF THE INVENTION

The composition of the invention can be prepared by mixing water and hydrofluoric acid in the above-noted amounts, employing distilled water when fresh water micro-organisms are to be examined and substituting filtered sea water for the distilled water when marine organisms are to be viewed.

In the method of using the solution of this invention, one drop of the aqueous suspension of the micro-organisms is placed, for instance, on a viewing surface such as a slide and with a pipette, or otherwise if desired, one drop of the solution is dropped into the center of the amount of specimen. Immobilization and staining of the motile organisms, or staining of immobile organisms is instantaneous, and the specimen is placed under a microscope and examined.

EXAMPLE 1

As an example of the composition of the invention, to 998 cc. of distilled water is added one cc. of a 49% by weight aqueous solution of hydrofluoric acid. There can be used, however, a 48% to 51% by weight aqueous solution of HF. One drop of the resulting test solution is added to one drop of a specimen of fresh water containing micro-organisms, and it is found that the micro-organisms are immediately immobilized and stained and their various structural features can be clearly seen under the microscope. Advantageously, one cc. of a 4% by weight aqueous solution of malachite green dye is also added to the test solution and viewing is still further improved, and the water portion of the drop is given an azure blue color.

EXAMPLE 2

In examining the miro-organisms of sea water, the formula of Example 1 is followed except that filtered sea water is used instead of distilled water in making up the test solution. Advantageously, malachite green is also added in the same manner as in Example 1 to give a turquoise color to the water of the drop. The micro-organisms are immobilized, where motile, and any micro-organisms present are also stained.

EXAMPLE 3

As another example of the solution of the invention, the following composition is prepared:

|  | Percent by Weight |
|---|---|
| Hydrofluoric acid (49% aq. soln.) | 0.049 |
| Malachite Green ($C_{23} H_{25} Cl \cdot N_2$) | 0.000345 |
| Water, distilled | 99.95 |
| Impurities, minor, including |  |
| Sulfate ($SO_4$) | 0.000000500 |
| Lead (Pb) | 0.000000050 |
| Nitrate ($NO_3$) | 0.000000500 |
| Iron (Fe) | 0.000000100 |
| Phosphate ($PO_4$) | 0.000000100 |
| Arsenic (As) | 0.000000005 |
| Copper (Cu) | 0.000000010 |
| Fluosilicic acid ($H_2SiF_6$) | 0.000010000 |
| Chloride (Cl) | 0.000000500 |
| Remainder, undetermined, to 100% |  |

The minor impurities noted above occur in the commercially available hydrofluoric acid and do not affect the essential characteristics and action of the solution of this invention.

One drop of a sample of fresh water containing protista, which are single cell organisms, is placed on a slide, and one drop of the above solution is pipetted into the center of the specimen. The two drops mix readily while quiescent and without mechanical agitation, and the protista are immediately immobilized and stained, while the aqueous medium is colored an azure blue. The features of the protista are not distorted or destroyed and can be viewed through a microscope with clarity and precision.

Where the micro-organisms are marine organisms, the solution is made up with filtered sea water instead of distilled water.

I have tried various quantities of HF in both fresh water and salt water. Using hydrofluoric acid in a concentration of 48% to 51%, I have found that the minimum quantity operative is 0.7 cc. per liter (0.035% HF) in the stock solution of distilled water, for use in fresh water containing the micro-organisms, whether or not the malachite green is present. The maximum operative amount is 2.0 cc. per liter (0.10% HF). In salt water I have succeeded in getting satisfactory results with as little as 0.5 cc. per liter of 48%–51% hydrofluoric acid (0.025% HF) and with as much as 2.5 cc. per liter (0.125% HF) of the salt water stock solution.

To observe motile and immotile micro-organisms simultaneously the above procedure is followed except that the drop of solution is brought into contact with a side area of the drop of suspension and mixes with a portion of the drop of suspension, instantly immobilizing any motile micro-organisms while the unmixed portion of the suspension retains motile micro-organisms, and the investigator can observe both motile and immotilized organisms simultaneously.

I claim:

1. A composition for staining micro-organisms to enable viewing by microscope and for immobilizing motile micro-organisms without damage to the structure thereof, which comprises an aqueous solution consisting essentially of water, from 0.025% to 0.125% by weight of hydrogen fluoride and a small amount of malachite green sufficient to provide a pleasing background color so that said micro-organisms stand out clearly.

2. A composition for staining fresh water micro-organisms and for immobilizing motile fresh water micro-organisms for microscopic examination consisting essentially of distilled water, from 0.035% to 0.10% by weight hydrogen fluoride and a small amount of malachite green sufficient to color said water azure blue.

3. A composition as in claim 2 containing about 0.05% by weight hydrogen fluoride.

4. A composition for staining marine micro-organisms and for immobilizing marine micro-organisms for microscopic examination consisting essentially of filtered sea water, from 0.025% to 0.125% by weight hydrogen fluoride and a small amount of malachite green sufficient to color said sea water turquoise.

5. A composition as in claim 4 containing about 0.05% by weight hydrogen fluoride.

6. A composition for staining micro-organisms and for immobilizing motile fresh water micro-organisms, being an aqueous solution consisting essentially of about 998 cc. distilled water, 1 cc. of a 48% to 51% by weight aqueous solution of hydrogen fluoride and 1 cc. of a 4% aqueous solution of malachite green.

7. A composition as in claim 6 containing 1 cc. of a 49% by weight aqueous solution of hydrogen fluoride.

8. A composition for staining micro-organisms and for immobilizing motile marine micro-organisms, being an aqueous solution consisting essentially of 998 cc. filtered sea water, 1 cc. of a 48% to 51% by weight of an aqueous solution of hydrogen fluoride, and 1 cc. of a 4% by weight aqueous solution of malachite green.

9. A composition as in claim 8 containing 1 cc. of a 49% by weight of an aqueous solution of hydrogen fluoride.

10. A method for preparing a specimen containing a number of micro-organisms in aqueous suspension for viewing under a microscope which comprises placing one drop of said suspension on a viewing surface, placing in contact with said drop of said suspension one drop of an aqueous solution containing 0.025% to 0.125% by weight hydrogen fluoride and a small amount of malachite green sufficient to provide a plea viewing color to said suspension and permitting said suspension and said solution to combine while quiescent, to stain said micro-organisms and to immobilize motile micro-organisms while maintaining their form and shape.

11. A method as in claim 10 wherein said solution contains about 0.05% by weight of hydrogen fluoride.

12. A method as in claim 10 wherein said micro-organisms are fresh water micro-organisms and said aqueous solution is a solution in distilled water, containing 0.035% to 0.10% HF.

13. A method as in claim 10 wherein said micro-organisms are marine organisms and said solution is a solution in filtered sea water.

14. A method as in claim 10 wherein said drop of said solution is placed centrally of the surface of said drop of said suspension.

15. A method as in claim 10 wherein said drop of said solution is placed in contact with the side of said drop of said suspension to immobilize only a portion of said micro-organisms.

* * * * *

UNITED STATES PATENT AND TRADEMARK OFFICE
CERTIFICATE OF CORRECTION

PATENT NO. : 4,161,514
DATED : July 17, 1979
INVENTOR(S) : Dee O. Casey

It is certified that error appears in the above-identified patent and that said Letters Patent are hereby corrected as shown below:

Column 4, line 3,

"miro-organisms" should read --micro-organisms--.

Column 6, line 14, "plea" should read --pale--.

Signed and Sealed this

Sixth Day of November 1979

[SEAL]

Attest:

RUTH C. MASON
Attesting Officer

LUTRELLE F. PARKER
Acting Commissioner of Patents and Trademarks